United States Patent [19]
Kuriakose et al.

[11] Patent Number: 4,724,191
[45] Date of Patent: Feb. 9, 1988

[54] BONDED HYDROGEN CONDUCTING SOLID ELECTROLYTES

[75] Inventors: Areekattuthazhayil K. Kuriakose, Napean; Thomas A. Wheat, Ottawa; Aftab Ahmad, Gloucester; Jon D. Canaday, Dunrobin; Albert J. Hanson, Ottawa, all of Canada

[73] Assignee: Minister of Energy Mines & Resources, Ottawa, Canada

[21] Appl. No.: 866,855

[22] Filed: May 12, 1986

[30] Foreign Application Priority Data

Jun. 28, 1985 [CA] Canada ................................. 485946

[51] Int. Cl.$^4$ ........................ H01M 8/10; H01M 8/00; C04B 35/10; C04B 35/16
[52] U.S. Cl. .................................... 429/193; 264/104; 264/122; 429/189; 429/191; 429/192; 501/153
[58] Field of Search ................ 264/104, 122; 429/189, 429/191, 192, 193; 501/153

[56] References Cited

U.S. PATENT DOCUMENTS 3,446,677  5/1969  Tennenhouse ...................... 429/193

FOREIGN PATENT DOCUMENTS 1180881  1/1985  Canada.
1191018  7/1985  Canada.
1213718  12/1986  Canada.
0147666  11/1984  European Pat. Off..
3,013,677  10/1981  Fed. Rep. of Germany.
3110571  9/1982  Fed. Rep. of Germany.

Primary Examiner—Jan H. Silbaugh
Assistant Examiner—Neil M. McCarthy
Attorney, Agent, or Firm—Mitches & Co.

[57] ABSTRACT

Hydronium bonded polycrystalline shaped articles may be produced by the simple expedient of selecting a hydronium containing powder prepared by one of a plurality of prior art methods and then intermingling the hydronium powder with ortho-phosphoric acid to obtain a viscous mixture (resembling the consistency of toothpaste). The mixture is then formed into a predetermined shape, for example a disc or tube, and the shaped polycrystalline ceramic is allowed to cure. Curing may take place at an elevated temperature below 100° C. for approximately 3 hours either as a step subsequent to forming, or as part of the forming step in 30 minutes at 120° C. The result is bonded hydrogen conducting - hydronium, $H_3O+$, solid rigid structure with a smooth finish copying the mold from which it was shaped. Specifically, the hydronium containing powders are selected from the group of poly antimonic acid and precursor powders generally known as Nasicons and preferably being selected from the group of powders consisting of sodium $\beta/\beta''$-alumina, sodium/potassium $\beta/\beta''$-alumina, sodium zirpsios, Gasicon and Yasicon.

15 Claims, No Drawings

BONDED HYDROGEN CONDUCTING SOLID ELECTROLYTES

This invention relates to the synthesis and fabrication of polycrystalline ceramic materials which conduct electricity by the mobility of hydrogen ions or hydronium ions and that are stable to temperatures above 100° C.

As such the invention concerns itself with the preparation of hydronium ion, $H_3O^+$, conducting crystalline powder by ion exchanging all or some of the $Na^+$ ions within a sodium conducting crystalline powder, with $H_3O^+$ ions and their subsequent fabrication into bonded dense bodies (hydronium ion conducting bonded polycrystalline solids).

Dense polycrystalline bodies of hydronium are thus capable of use as a membrane in devices such as hydrogen fuel cells, hydrogen detectors, and steam electrolysers.

BACKGROUND OF THE INVENTION

There are a variety of known hydronium conducting compounds, and their crystalline powder form is well known as is their fabrication. We have conceived of a method of bonding such hydronium conducting crystalline powders into dense strong bodies with a hydronium conducting adhesive without affecting the ionic conductivity significantly, thus eliminating laborious steps that are required to preserve the integrity of the precursor, ie. Nasicon powders such as various sodium polycrystalline compounds that are generally known as precursor compounds to their hydronium analogue.

A commonly known hydronium conductor is hydronium-$\beta''$-alumina ($H_3O^+$-$\beta''$-$Al_2O_3$). It is a superior conductor of protons, though relatively simple to form, as a powder, from the precursor form $Na^+$-$\beta/\beta''$-$Al_2O_3$, it is difficult to fabricate into the preferred polycrystalline rigid form that is the preferred form to be used as the solid electrolyte in fuel cells or in other devices which utilize hydronium-$\beta''$-alumina as a proton conducting membrane. Although a sodium ion conducting $\beta''$-alumina can be fabricated into polycrystalline dense bodies by sintering, in spite of its affinity for hydrogen ions, on ion exhange of the $Na^+$ by protons or hydronium ions the polycrystalline bodies tend to shatter into powder again. This shattering is attributed to the smaller interstitial spaces occupied by the sodium ion, within the molecule of Na-$\beta''$-alumina, that is to be replaced by the dimensionally larger hydronium ions. It is known that the dimensional size of the sodium ion $Na^+$, is 0.9 Å, while the hydronium, $H_3O^+$ is 1.4 Å.

In another aspect, the invention relates to other hydronium conducting powders, and their respective bonding into a hydronium conducting polycrystalline solid ceramic electrolyte in a manner as will become apparent.

As an object thereof, a crystalline powder form of sodium-$\beta''$-alumina is subjected to hydronium ion exchange while still a powder form. The macroscopic shattering problem does not arise because the individual particles are either single crystals or single crystal aggregates in as powder and when the smaller sodium ion is replaced, during ions exchange, by the larger hydronium ion, the lattice structure of each molecule accordingly expands and because those molecules are aggregated in powder form, the powder is able to accommodate the expansion. Even if some "shattering" takes place the resultant is powder still.

We have conceived a method for bonding crystalline powder of hydronium-$\beta''$-alumina into dense strong bodies without affecting the ionic conductivity significantly, thus eliminating all the laborious steps that are required in the prior art to produce such product.

As another object of the invention the sodium super ionic conductors ($Na_5ReSi_4O_{12}$ where Re=Y or Gd) or sodium Zirconium phospho silicate subnom. Nazirpsio [1, 2] are subjected to ion exchange, by known methods, so that either all or part of the sodium ion is replaced with a hydronium ion whereby to create a hydronium conducting powder.

These hydronium powders are subject, according to methods of our invention, to bonding whereby to create a solid hydronium conducting electrolyte hence a bonded hydrogen ion conducting solid electrolyte.

PRIOR ART

According to the present knowledge hydronium conducting $\beta/\beta''$-aluminas in the form of a solid electrolyte may be fabricated as a dense ceramic, for example, by either (a) direct ion exchange of a sintered sodium $\beta''$-alumina in potassium oxide vapor at 1400° C. in an all platinum vessel followed by boiling in concentrated sulphuric acid to form the hydronium analogue, [3] or, (b) sintering of a mixed sodium/potassium $\beta/\beta''$-alumina powder followed by potassium ion exchange in a potassium chloride or nitrate molten bath [4, 5] and a following substitution of $Na^+/K^+$ during final ion exchange by hydronium, to achieve the hydronium form by a field-assisted ion exchange (FAIE) technique in dilute acid at about 90° C. [6].

According to these procedures they are multi-stage processes that are difficult and time consuming. Often the products tend to crack resulting in a low yield. This cracking is accompanied by low strength which is undesirable for some of the intended applications. Also, in the FAIE stage, only a partial exchange of the sodium and potassium ions by the hydronium ions is achieved; otherwise the material develops cracks during extended ion exchange. Another requirement in the process (b) is to retain a high proportion (>60%) of $\beta\delta$ phase in the sintered sodium/potassium material in order to have high ionic conductivity after hydronium ion exchange. This requires very stringent control of the powder preparation, calcination and sintering stages.

As is known in the prior art, the stability of hydronium-containing $\beta/\beta''$-alumina materials is poor above about 500° C. rendering the formation of cohesive bodies by any form of high temperature sintering process impossible.

Known procedures, particularly that developed by Hong, [7] have produced a series of powders based on sodium zirconium phospho silicate subnom. Nazirpsios having the general formula:

$$Na_{1+x}Zr_2SiP_{3-x}O_{12}$$

Max Planck Institute [8] have developed a modified version of Nazirpsio according to the following formula:

$$Na_{1+x}Zr_{2-x/3}Si_xP_{3-x}O_{12-2x/3}$$

Accordingly, for the purposes of this disclosure, Nazirpsios shall be either of the aforesaid analogues or their respective mixtures. The Nazirpsios therefore may be represented by the general formula:

$$Na_{1+x}Zr_{2-\frac{nx}{3}}Si_xP_{3-x}O_{12-\frac{2nx}{3}}$$

where $0 = \% \ n = 1$ and $x = 0 = 3$

Further, the aforesaid inventive method of bonding has application to other Hydrogen conducting forms of Nasicons Yasicon (sodium yttrium silicate) or Gasicon (sodium gadolinium silicate).

THE INVENTION

In one aspect, we have developed a process for the direct production of a hydronium $\beta''$-alumina powder virtually free of the related hydronium $\beta$-alumina form. The hydronium-$\beta''$-alumina powder may be bonded into dense strong bodies which retain their affinity for protons to temperatures in excess of 100° C.

This process has advantage as it avoids the need to produce an intermediate sodium/potassium sintered precursor material having an $f(\beta) \doteq 0.4$ [5] as is required by the prior art [5, 6, 9]. The achievement of an $f(\beta) \doteq 0.4$ [5, 6, 9] in the dense sintered precursor material containing both sodium and potassium is very difficult (time consuming involving many laborious steps).

This invention contemplates the use of precursor powders having mixtures of X-$\beta/\beta''$-alumina produced by the known spray drying or freeze drying processes [4, 5, 6] or any other processes [1, 2, 3, 10] then calcining them to X-9$\beta/\beta''$-alumina mixtures having a concentration of $\beta''$ between 1% and 99% (by weight).

It further contemplates the treatment of the calcined powder with an acidic solution to create a hydronium containing $\beta/\beta''$-alumina solid, powder or compound $(H_3O^+, X)$-$\beta/\beta''$-$Al_2O_3$ where X is a cation, preferably and may be $Na^+$ where there is no complete ion exchange. We, however, can easily achieve complete ion exchange of $Na^+$ as will become apparent.

This invention contemplates a quicker and simpler method for the formation of dense, cohesive bodies than is revealed in the prior art.

It also contemplates the fabrication of hydronium conductive bodies of diverse shapes while avoiding any high temperature sintering stages required by the prior art.

It further contemplates the use of other hydronium containing solids in powder form.

The invention contemplates the use of a hydronium conducting boding agent selected from the group of bonding agents comprising hydronium conducting organic polymers and phosphates.

It further envisages the use of aluminium hydrogen phosphates as a conductive bonding agent for hydronium containing powders.

It also envisages the use of zirconium hydrogen phosphates as a conductive bonding agent for hydronium containing powders thereby binding them into solid polycrystalline bodies.

The invention further envisages the use of phosphorus containing compounds known to be insoluble in water for the bonding of hydronium ion conducting powders, whether aluminas of phospho silicates, into solid polycrystalline electrolyte ceramics.

The invention therefore achieves a method of chemically bonding hydronium ion conducting solid electrolyte powder into dense polycrystalline shaped bodies comprising the steps of:

(a) selecting a hydronium containing powder and a bonding agent selected from the group of bonding agents comprising hydronium conducting organic polymers and phosphates;

(b) intermingling the hydronium powder with the bonding agent to obtain a mixture;

(c) forming the mixture into a predetermined shape;

(d) curing the predetermined shape so as to create a dense polycrystalline shaped hydronium conducting ceramic.

More particularly, the invention therefore achieves a method of chemically bonding hydronium ion conducting solid electrolyte powder into dense polycrystalline shaped bodies comprising the steps of:

(a) selecting a hydronium containing powder;

(b) intermingling the hydronium powder with orthophosphoric acid to obtain a mixture;

(c) forming the mixture into a predetermined shape;

(d) curing the predetermined shape so as to create a dense polycrystalline shaped hydronium conducting ceramic.

The invention also contemplates that the hydronium containing powder selected in step (a) as aforesaid, is selected from the group of materials comprising $$X-\beta/\beta''-Al_2O_3;$$

$$J-Zr_{(2-nx/3)}Si_xP_{3-x}O_{(12-2nx/3)}J-ReSi_4O_{12};$$

and, $$Sb_2O_5 \cdot mH_2O$$

where $X = Na^+/K^+/H_3O^+$, or $Na^+/H_3O^+$, or $H_3O^+$; $J = Na^+/H_3O^+$; $0 \leq n \leq 1$; $Re = Y$ or $Gd$; and $(0.5 \leq m \leq 6)$.

The invention also contemplates a hydronium ion conducting bonded polycrystalline solid, snow white in colour, very difficult to break by hand and with good resistance to breaking, shattering and cracking and having a conductivity at 100° C. between $1.4 \times 10^{-4}$ (ohm cm)$^{-1}$ and $6.0 \times 10^{-4}$ (olm cm)$^{-1}$ wherein 50% to 90% by weight is the hydronium conducting phase, the balance an ionic bonding agent. Specifically, the ionic bonding agent is an ion conducting polymer, or a hydrogen phosphate, while the hydronium conducting phase is $H_3O^+$-$\beta/\beta''$-$Al_2O_3$ or hydronium Zirpsio or hydronium Gasicon or hydronium Yasicon or poly antimonic acid.

The invention will now be described by way of examples, there being no drawings.

EXAMPLE 1

A precursor powder for sodium $\beta/\beta''$-alumina is prepared by spray-drying a slurry containing finely divided alpha alumina in a solution of bicarbonates of sodium and magnesium in required proportions according to known procedures [11]. The powder is then calcined at 1300°–1700° C. to obtain a sodium $\beta/\beta''$-alumina powder containing 80–90% of $\beta''$-alumina. 20 g of this powder is refluxed with 1.5 L of of 0.1N hot (approximately 100° C.) hydrochloric acid diluted slightly in water, in a 2 L round bottom flask for 4–6 hours. Exchange of the sodium ions by hydronium ions takes place during this process. The contents are allowed to cool to room temperature and then transferred into a 2 L beaker and the residue is allowed to settle then filtered by decantation. The residue is washed in distilled water and dried in an air oven at about 90° C. to yield the hydronium $\beta/\beta''$-alumina powder.

An X-ray diffraction pattern showed that the product was about 90% $\beta''$-alumina, balance $\beta$-alumina. A small fraction of the product after heat treatment at 800° C. showed no X-ray pattern for $\beta$ or $\beta''$-alumina, but only broad peaks corresponding to gamma-type alumina. This proves that the product after exchange in hot acid was hydronium $\beta/\beta''$-alumina; $H_3O^+$-$\beta/\beta''$-$Al_2O_3$. (If the product had been sodium $\beta/\beta''$-alumina, the $\beta''$ phase would not have decomposed at 800° C.).

In one procedure, 1.5 g of the hydronium $\beta/\beta''$-alumina powder produced as aforesaid was ground with 0.6 g of orthophosphoric acid in an alumina mortar and the resulting mixture was white and slightly more viscous than toothpaste. The mixture was pressed in a 2.5 cm diameter steel die with Teflon lining and Teflon caps at a pressure of about 14 KPa. The pellet was removed from the die and held in an air oven at about 80° C. for 3 hours. It formed a hard disc of density 2.8 g/mL as measured from the physical dimensions.

In another procedure, the hydronium-$\beta''$-alumina phosphoric acid mixture, prepared as above, was pressed into a Teflon lined die and heated under pressure at about 14 KPa and 120° C. for 30 min. A hard disc of density 3.08 g/mL was obtained. The disc had a smooth surface mirroring that of the die, was snow white in colour, very difficult to break by hand and when dropped onto a wooden floor from the height of about 1½ meters, the disc did not break, shatter, nor crack, nor was it otherwise visibly damaged. These physical properties were achieved by either of the aforesaid 2 procedures.

EXAMPLE 2

A sodium zirpsio ($Na_{1+x}Zr_2Si_xP_{3-x}O_{12}$ or $Na_{1+x}Zr_{2-x/3}Si_xP_{3-x}O_{12-2x/3}$) subnom.: Nazirpsio, precursor powder is prepared by any known method [7, 8, 12, 13]. The resultant powder is calcined at a temperature below its sintering temperature (1100° C.-1200° C.) for about 30 min. A slight caking of the powder takes place during this heat treatment and the powder is converted into fine crystals of Nazirpsio. An X-ray diffraction pattern of the powder is made in order to assure that the power has undergone reaction to form the zirpsio. The Nazirpsio powder (15 g sample) is refluxed with 0.1N hydrochloric acid (1.5 L) as in example 1 for about 6 hours. The replaceable sodium ions in the Nazirpsio are exchanged by hydronium ions during this operation to form hydronium zirpsio ($H_3O^+$-zirpsio). (if a sintered piece of Nazirpsio is used for this exchange, it breaks apart into a large number of small pieces). The solid product is washed with distilled water, filtered and dried in an oven at about 90° C. An X-ray diffraction pattern of the hydronium zirpsio in which the "a" and "c" directions of the rhombohedral Nazirpsio crystal lattice are respectively contracted and expanded is obtained which confirms the hydronium ion exchange of the product.

A 1.5 g of the hydronium zirpsio powder is mixed with 0.6 g of ortho phosphoric acid diluted slightly in water and is pressed in a Teflon ® lined steel die approximately 2.5 cm in diameter at about 14 KPa at 120° C. for 30 min. A dense hard disc of bonded hydronium zirpsio is obtained. The physical properties of the disc were similar to that of Example 1.

EXAMPLE 3

Instead of sodium $\beta/\beta''$-alumina or Nazirpsio in example 1 and 2 respectively, a sample of Gasicon, $Na_5GdSi_4O_{12}$, is prepared by known methods [10] and is then used for refluxing with a hot hydrochloric acid. The resultant hydronium formed is dried as aforesaid; then, bonded as in Examples 1 and 2, with the said phosphoric acid. The resultant dense hard disc had the same physical properties as in the earlier examples.

EXAMPLE 4

Similarly, in a like procedure as in Example 2, a sample of Yasicon; $Na_5YSi_4O_{12}$, prepared by the known methods [10] is then used for refluxing with a hot hydrochloric acid. The resultant hydronium formed is dried as aforesaid then bonded as in Examples 1 and 2, with the said phosphoric acid. The resultant dense hard disc had the same physical properties as in the earlier examples.

EXAMPLE 5

Poly antimonic acid, a hydronium conductor in powder form, was mixed with ortho phosphoric acid and processed as aforesaid, then pressed in a Teflon ® lined steel die of approximately 2.5 cm in diameter and at about 14 KPa at 100° C. for 30 minutes. Once again the same snow white hard disc now of bonded poly antimonic acid was obtained.

Conductivity Results

Typical conductivity results of some of the products obtained according to the examples are given for various temperatures as per the following table:

$H_3O^+$-$\beta/\beta''$-alumina bonded hard disc (fabricated as per Example 1 according to either of the curing procedures)

| 25° C. | 50° C. | 75° C. | 100° C. | |
|---|---|---|---|---|
| $1.0 \times 10^{-5}$ | $1.0 \times 10^{-4}$ | $4.8 \times 10^{-4}$ | $5.9 \times 10^{-4}$ | |
| $1.9 \times 10^{-7}$ | $1.9 \times 10^{-6}$ | $2.4 \times 10^{-5}$ | $1.4 \times 10^{-4}$ | (ohm cm)$^{-1}$ |

Nazirpsios (Hong Composition) as per Example 2

| | 25° C. | 50° C. | 75° C. | 100° C. | |
|---|---|---|---|---|---|
| x = 1.5 | $2.3 \times 10^{-4}$ | $6.6 \times 10^{-4}$ | $9.3 \times 10^{-4}$ | $1.0 \times 10^{-3}$ | |
| x = 2.2 | $2.1 \times 10^{-5}$ | $8.6 \times 10^{-5}$ | $1.5 \times 10^{-4}$ | $1.9 \times 10^{-4}$ | (ohm cm)$^{-1}$ |

Nazirpsios (Max Planck Institute Composition) as per Example 2

| | 25° C. | 50° C. | 75° C. | 100° C. | |
|---|---|---|---|---|---|
| x = 2.0 | $1.9 \times 10^{-5}$ | $3.3 \times 10^{-5}$ | $1.1 \times 10^{-4}$ | $1.7 \times 10^{-4}$ | (ohm cm)$^{-1}$ |

In each of the aforesaid compositions there is a phosphate which is formed as a result of curing and acts as the hydronium conducting ionic binding agent with the individual crystals of the powder whose precursor was the Nasicon. Thus in Example 1, the dense hard disc has a chemical composition where 50% to 85% by weight is $H_3O^+$-$\beta/\beta''$-$Al_2O_3$ and the balance alumina hydrogen phosphate.

In Example 2 between 50% and 90% of the dense hard disc is hydronium zirpsio and the balance zironium hydrogen phosphate. Similarly, the hard disc of Examples 3 and 4 are 50% to 90%, respectively, hydronium Gasicon and hydronium Yasicon respectively, the balance Gadolinium and Yttrium acid phosphate and for Example 5, 50% to 90% is poly antimonic acid; the balance by weight antimonic hydrogen phosphate.

REFERENCES

1. Federal Republic of Germany patent DE No. 3013677 issued Oct. 15, 1981 to Hans Hoefer, Michael A. Bell and Albrecht Rabenau "HYDROGEN CONDUCTING COMPOUNDS AND THEIR USE AS SOLID ELECTROLYTES".
2. Federal Republic of Germany patent DE No. 3110571 issued Sept. 30, 1982 to Albrecht Rabenau, Hans Hoefer, and Michael F. Bell "HYDROGEN CONDUCTING COMPOUNDS AND THEIR USE AS SOLID ELECTROLYTES IN ELECTRO CHEMICAL CELLS".
3. U.S. Pat. No. 3,446,677 issued May 27, 1969 by Gerald J. Tennenhouse "Method of Making Solid Ionic Conductors".
4. Canadian Pat. No. 1,180,881 issued Jan. 15, 1985 by P. S. Nicholson, T. A. Wheat and M. Nagai entitled "THE PREPARATION OF A PRECURSOR POWDER FOR THE MANUFACTURE OF A CERAMIC HYDROGEN ION CONDUCTOR.
5. Canadian Pat. No. 1,191,018 issued July 30, 1985 entitled "THE PREPARATION OF A PRECURSOR SOLID FOR THE MANUFACTURE OF A CERAMIC HYDROGEN ION CONDUCTOR" by inventors Michael Francis Bell; Patrick Stephen Nicholson; Michael Sayer, Kimihiro Yamashita, Masayuki Nagai and David Stanley Smith.
6. European Patent application, publication No. 0147666, entitled "METHOD OF CONVERTING A PRECURSOR CERAMIC SOLID INTO A SOLID CERAMIC HYDRONIUM CONDUCTOR" by inventors Michael Francis Bell; Patrick Stephen Nicholson; Michael Sayer and Kimihiro Yamashita published July 10, 1985.
7. H.Y-P. Hong "Crystal Structure and Crystal Chemistry in the System" $Na_{1+x}Zr_2Si_xP_{3-x}O_{12}$. Material Research Bulletin, Volume 11(2), 197–182, 1976.
8. Von Alpen, M. F. Bell, H. H. Hoeffer "Compositional Dependence of the Electro-chemical and Structure Parimeters in the Nasicon System". Solid State Ionics, Volume 3-4, Pages 215–18, 1981.
9.

$$f(\beta) = \frac{\beta}{\beta + \beta''}$$

10. Canadian Pat. No. 1,213,718, issued Dec. 11, 1986 by Patrick Stephen Nicholson and Kimihiro Yamashita "SILICATE SUPERIONIC CONDUCTORS AND METHOD OF MAKING THE SAME".
11. A. Ahmad, T. A. Wheat, A. K. Kuriakose and B. Kindl Sodium Beta"-Aluminas by Aqueous Spray Drying" Jour. Can. Ceram. Society, Vol 52, 1–7, 1983.
12. H. H. Quon, T. A. Wheat and W. Nesbitt "Systhesis, Characterization and Fabrication of $Na_{1+x}Zr_2P_{3-x}O_{12}$" Materials Research Bulletin, Vol 15(11), 1533–1539, 1980.
13. A. K. Kuriakose, T. A. Wheat, A. Ahmad and J. DiRocco "Synthesis, Sintering and Microstructure of Nasicons" Journal American Ceramic Society, Vol 67(3), 179–183, 1984.

The embodiments of the invention in which an exclusive property or privilege is claimed are defined as follows:

1. A method of chemically bonding hydronium ion conducting solid electrolyte powder into dense polycrystalline shaped bodies comprising the steps of:
   (a) selecting a hydronium containing powder and a bonding agent selected from the group of bonding agents consisting of hydronium conducting organic polymers and phosphates;
   (b) intermingling the hydronium powder with the bonding agent to obtain a mixture;
   (c) forming the mixture into a predetermined shape;
   (d) curing the predetermined shape so as to create a dense polycrystalline shaped hydronium conducting ceramic body, in which the bonding agent does not affect the hydronium ion conductivity significantly.

2. A method of chemically bonding hydronium ion conducting powder into dense polycrystalline shaped bodies comprising the steps of:
   (a) selecting a hydronium containing powder;
   (b) intermingling the hydronium powder with orthophosphoric acid bonding agent to obtain a mixture;
   (c) molding the mixture into a predetermined shape;
   (d) curing the predetermined shape so as to create a dense polycrystalline shaped hydronium ceramic body, in which the bonding agent does not affect the hydronium ion conductivity significantly.

3. The method as claimed in claim 2, wherein the intermingling step (b) includes intermingling the hydronium powder with ortho phosphoric acid and water to obtain a paste like mixture.

4. The method as claimed in claim 2, wherein the hydronium containing powder is selected from the group of powders converted into hydronium powder from precursor powders consisting of sodium $\beta/\beta''$-alumina, sodium/potassium $\beta/\beta''$-alumina, sodium zirpsios, Gasicon, Yasicon and poly antimonic acid.

5. The method as claimed in claim 3, wherein the hydronium containing powder is selected from the group of powders converted into hydronium powder from precursor powders consisting of sodium $\beta/\beta''$-alumina, sodium/potassium $\beta/\beta''$-alumina, sodium zirpsios, Gasicon, Yasicon and poly antimonic acid.

6. The method as claimed in claim 2, 3, or 4, wherein the amount of ortho phosphoric acid in gravimetric ratio with the hydronium powder is between 15%–30% by weight of the mixture.

7. The method as claimed in claim 5, wherein the amount of ortho phosphoric acid in gravimetric ratio with the hydronium powder is between 15%–30% by weight of the mixture.

8. The method as claimed in claim 1, 2 or 3, wherein the selecting step (a) a material is selected from the group of materials consisting of $X-\beta/\beta''-Al_2O_3$;

$J-Zr_{(2-nx/3)}Si_xP_{3-x}O_{(12-2nx/3)}J-ReSi_4O_{12}$;

and, $Sb_2O_5 \cdot mH_2O$ where $X = Na^+/K^+/H_3O^+$, or $Na^+/H_3O^+$, or $H_3O^+$; $J = Na^+/H_3O^+$; $0 < n < 1$; $Re = Y$ or $Gd$; and $(0.5 < m < 6)$.

9. A hydronium ion conducting bonded polycrystalline solid, snow white in colour, very difficult to break by hand and with good resistance to breaking, shattering and cracking and having a conductivity at 100° C. between $1.4 \times 10^{-4}$ (ohm cm)$^{-1}$ and $6.0 \times 10^{-4}$ (ohm cm)$^{-1}$ wherein 50% to 90% by weight is hydronium conducting powder, the balance an ionic bonding agent.

10. The bonded polycrystalline solid as claimed in claim 9, wherein the ionic bonding agent is a hydrogen phosphate.

11. The bonded polycrystalline solid as claimed in claim 9, wherein the hydronium conducting powder is $H_3O^+$-$\beta/\beta''$-$Al_2O_3$ and the balance is alumina hydrogen phosphate.

12. The bonded polycrystalline solid as claimed in claim 9, wherein the hydronium conducting powder is hydronium Zirpsio and the balance is zirconium hydrogen phosphate.

13. The bonded polycrystalline solid as claimed in claim 9, wherein the hydronium conducting powder is selected from the group of materials consisting of hydronium Gasicon, hydronium Yasicon and the balance is selected from the group of materials consisting of Gadolinium acid phosphate and Yttrium acid phosphate.

14. The bonded polycrystalline solid as claimed in claim 9, wherein a presursor powder for the hydronium conducting powder is poly antimonic acid and the balance is antimonic hydrogen phosphate.

15. The bonded polycrystalline solid as claimed in claim 9, wherein the ionic bonding agent is a polymer.

* * * * *